United States Patent
Lad

(10) Patent No.: US 10,293,015 B1
(45) Date of Patent: May 21, 2019

(54) COMPOSITION FOR TREATING SKIN DERMATOSES

(71) Applicant: EXELTIS USA DERMATOLOGY, INC., Chatham, NJ (US)

(72) Inventor: Babu Lad, Florham Park, NJ (US)

(73) Assignee: PARAGON NORDIC AB, Vallentuna (SE)

( * ) Notice: Subject to any disclaimer, the term of this patent is extended or adjusted under 35 U.S.C. 154(b) by 0 days.

(21) Appl. No.: 16/104,620

(22) Filed: Aug. 17, 2018

(51) Int. Cl.
| | |
|---|---|
| *A61K 31/01* | (2006.01) |
| *A61K 36/87* | (2006.01) |
| *A61K 31/80* | (2006.01) |
| *A61K 31/164* | (2006.01) |
| *A61K 47/02* | (2006.01) |
| *A61K 47/10* | (2017.01) |
| *A61K 47/12* | (2006.01) |
| *A61K 47/26* | (2006.01) |
| *A61K 31/19* | (2006.01) |

(52) U.S. Cl.
CPC ............. *A61K 36/87* (2013.01); *A61K 31/01* (2013.01); *A61K 31/164* (2013.01); *A61K 31/19* (2013.01); *A61K 31/80* (2013.01); *A61K 47/02* (2013.01); *A61K 47/10* (2013.01); *A61K 47/12* (2013.01); *A61K 47/26* (2013.01)

(58) Field of Classification Search
CPC ........ A61Q 19/00; A61Q 19/08; A61Q 19/02; A61Q 17/04; A61K 47/14; A61K 47/26; A61K 47/34; A61K 8/0212; A61K 8/0652
See application file for complete search history.

(56) References Cited

U.S. PATENT DOCUMENTS

2014/0154195 A1* 6/2014 Mohammadi ............ A61K 8/37
424/63

* cited by examiner

*Primary Examiner* — Nannette Holloman
(74) *Attorney, Agent, or Firm* — Oblon, McClelland, Maier & Neustadt, L.L.P.

(57) ABSTRACT

Compositions including water, petrolatum, dimethicone, glycerrhetinic acid, at least one ceramide, at least one C2-C5 alkanol substituted with two to four hydroxyl groups, at least one N-acylethanolamine, and grape seed extract comprising proanthocyanidin, as well as methods of treating skin dermatoses and/or reducing symptoms associated with skin dermatoses using such compositions, are provided.

17 Claims, No Drawings

COMPOSITION FOR TREATING SKIN DERMATOSES

FIELD OF THE INVENTION

The present invention relates to compositions comprising water, petrolatum, dimethicone, glycerrhetinic acid, at least one ceramide, at least one C2-C5 alkanol substituted with two to four hydroxyl groups, at least one N-acylethanolamine, and grape seed extract comprising at least one proanthocyanidin. These compositions are useful for treating skin dermatoses and/or reducing symptoms associated with skin dermatoses, in particular atopic dermatitis and/or allergic contact dermatitis.

DISCUSSION OF THE BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The skin is an organ which provides a physiological barrier between a person and the environment by preventing entrance of foreign substances including biological, chemical, and physical assaults, as well as exit of excessive amount of water. The stratum corneum, which is the outermost layer of the skin, has corneocytes embedded in a structurally organized lipid matrix primarily composed of ceramides, cholesterol, and fatty acids. However, if depletion of ceramide, cholesterol or free fatty acids occurs, the lipid bilayers may become disorganized and lead to abnormal function of the skin barrier.

Dermatitis/Dermatoses is/are superficial inflammation of the skin characterized by one or more of erythema (redness), pruritus (itchiness), excoriation (scratches, scabs), papulation (bumpiness), edema (swelling), and oozing. Different causes of dermatoses can range from allergic reactions to external substances, as in contact dermatitis, to internal causes as in atopic dermatitis. Traditionally, treatment of such dermatoses generally involves prescription strength corticosteroids, which have well-known detrimental side effects such as thinning of the skin, stretch marks, skin coloration, and reduced immune defense resulting in a secondary bacterial infection. Further, prolonged use of corticosteroids is not recommended, especially among children and pregnant women, as systemic side effects may occur.

Individuals with dermatoses generally have an impaired stratum corneum, leading to skin barrier dysfunction. An impaired skin barrier associated with dermatitis has a heightened susceptibility to penetration of external irritants and allergens, and an increased propensity for skin irritation and inflammation.

There remains a need for topical compositions that can treat skin dermatoses and/or reduce symptoms associated with skin dermatoses, in particular atopic dermatitis and/or allergic contact dermatitis.

SUMMARY OF THE INVENTION

The present invention relates to compositions comprising water, petrolatum, dimethicone, glycerrhetinic acid, at least one ceramide, at least one C2-C5 alkanol substituted with two to four hydroxyl groups, at least one N-acylethanolamine, and grape seed extract comprising at least one proanthocyanidin. These compositions are useful for treating skin dermatoses and/or reducing symptoms associated with skin dermatoses, in particular atopic dermatitis and/or allergic contact dermatitis.

The present invention also relates to methods of treating one or more skin dermatoses, in particular atopic dermatitis and/or allergic contact dermatitis, comprising topically administering compositions comprising water, petrolatum, dimethicone, glycerrhetinic acid, at least one ceramide, at least one C2-C5 alkanol substituted with two to four hydroxyl groups, at least one N-acylethanolamine, and grape seed extract comprising at least one proanthocyanidin to the one or more skin dermatoses in an amount sufficient to treat the one or more skin dermatoses.

The present invention also relates to methods of reducing at least one symptom associated with one or more skin dermatoses, in particular atopic dermatitis and/or allergic contact dermatitis, comprising topically administering compositions comprising water, petrolatum, at least one dimethicone, glycerrhetinic acid, at least one ceramide, at least one C2-C5 alkanol substituted with two to four hydroxyl groups, at least one N-acylethanolamine, and grape seed extract comprising at least one proanthocyanidin to the one or more skin dermatoses in an amount sufficient to reduce the at least one symptom associated with the one or more skin dermatoses.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

As used herein, the words "a" and "an" mean "one or more".

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former" or "film forming agent" or "film forming polymer" or "film forming resin" as used herein mean a polymer or resin that leaves a film on the substrate to which it is applied, for example, after a solvent accompanying the film former has evaporated, absorbed into and/or dissipated on the substrate. "Film Former" does not include occlusive agents.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Substantially free of" or "substantially devoid of" as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of film former" or "devoid of film former" means that film formers (as defined above) are omitted (that is 0% by weight). "Substantially free of film former" or "substantially devoid of film former" means that film former can be present in the composition at an amount of less than about 0.25% by weight. "Essentially free of film former" or "essentially devoid of film former" means that film former can be present in the composition at an amount of less than about 0.1% by weight. All weights herein refer to weight % based on the total weight of the composition.

The compositions and methods of the present invention can "comprise," "consist of" or "consist essentially of" the essential elements and limitations of the invention described herein, as well as any additional or optional ingredients, components, or limitations described herein or otherwise useful.

For purposes of the compositions and methods of the present invention where the invention "consists essentially of" the identified ingredients, elements and/or process steps, the "basic and novel property" of such ingredients, elements and/or methods will be identified in the ingredient, element or method step. For example, where the ingredient or element is an "inflammation reduction component," the basic and novel property is "inflammation reduction." Also, where the ingredient or element is a "stratum corneum water-holding-ability component," the basic and novel property is "water-holding-ability." Further, where the ingredient or element is an "itch reduction component," the basic and novel property is "itch reduction." Also, where the ingredient or component is an "occlusion component," the basic and novel property is "occlusion."

Compositions of the Present Invention

According to the present invention, compositions comprising water, petrolatum, dimethicone, glycerrhetinic acid, at least one ceramide, at least one C2-C5 alkanol substituted with two to four hydroxyl groups, at least one N-acylethanolamine, and grape seed extract comprising at least one proanthocyanidin are provided.

Preferably, the medium or base for the compositions of the present invention and the methods of composition preparation are similar to those disclosed in U.S. Pat. No. 5,993,830, the entire contents of which is hereby incorporated by reference. Such compositions are capable of creating a semi-permeable membrane in the skin. Compositions of the present invention are capable of forming a semi-occlusive dressing after application. Exemplary additional ingredients which can be added to the compositions of the present invention are discussed below.

Compositions of the present invention can be in any form suitable for topical application. For example, compositions of the present invention can in the form of an ointment, a cream, a gel, a lotion, a suspension, a foam, an aerosol spray, a transdermal patch, or other form known to one of ordinary skill in the art. Preferably, compositions of the present invention are in the form of a cream or an ointment.

Preferably, compositions of the present invention have a viscosity of from about 1,000 to about 500,000 centipoise (cps), about 5,000 to about 250,000 cps, about 10,000 to about 100,000 cps, about 10,000 to about 50,000 cps, or about 15,000 to about 25,000 cps at a temperature of 25° C. Viscosities may be measured using a viscometer under conditions generally known in the art.

Preferably, compositions of the present invention have a pH of 4-8, preferably 4.5-7.5, preferably 5-7, and preferably 5.5-6.5 at a temperature of 25° C. pH value of the composition may be measured using a pH meter as is known in the art.

Preferably, the compositions are substantially free, essentially free or free of film forming agents. In particular, it is preferred that the compositions are substantially free, essentially free or free of homopolymers and copolymers containing polyvinylpyrrolidone.

Water

According to the present invention, compositions comprising water are provided. Preferably, water is present in an amount ranging from about 50% to about 85% by weight, preferably from about 60% to about 80% by weight, preferably from about 70% to about 75% by weight, and preferably from 71% to 72% by weight, all weights being based on the total weight of the composition, including all ranges and subranges therebetween. Preferably, the composition is in the form of an emulsion, preferably an oil-in-water emulsion.

Petrolatum

According to the present invention, compositions comprising petrolatum are provided. Preferably, petrolatum is present in an amount less than 20% by weight, preferably less than about 10% by weight, preferably less than about 6% by weight, but greater than about 1% by weight, preferably greater than about 3% by weight, and preferably greater than about 4% by weight, all weights being based on the total weight of the composition, including all ranges and subranges such as, for example, from about 1% to about 10% by weight and from about 4% to about 6% by weight, with about 5% being a preferred amount.

Although not wishing to be bound by any theories, petrolatum is believed to function as an occlusive agent to help create a semi-occlusive film on skin after topical application which can help form a barrier to inhibit evaporative loss of moisture from the body and protect the skin against environmental irritants.

Dimethicone

According to the present invention, compositions comprising dimethicone (polydimethylsiloxane) are provided. Preferably, dimethicone is present in an amount less than 20% by weight, preferably less than about 10% by weight, preferably less than about 6% by weight, but greater than about 1% by weight, preferably greater than about 3% by weight, and preferably greater than about 4% by weight, all weights being based on the total weight of the composition, including all ranges and subranges such as, for example, from about 1% to about 10% by weight and from about 4% to about 6% by weight, with about 5% being a preferred amount.

Although not wishing to be bound by any theories, dimethicone, like petrolatum, is believed to function as an occlusive agent to help create a semi-occlusive film on skin after topical application which can help form a barrier to inhibit evaporative loss of moisture from the body and protect the skin against environmental irritants.

Dimethicone can have different viscosity characteristics depending upon the amount of repeating units within the compound. Accordingly, it should be understood that "dimethicone" as used herein encompasses one or more dimethicone compounds having different viscosity characteristics. Thus, "dimethicone" encompasses not only a single dimethicone having a single viscosity, but also multiple dimethicones having varying viscosities. Preferably, the one or more dimethicones in the compositions of the present invention have a viscosity of from about 100 to about 5,000,000 cps, preferably from about 1,000 to about 2,500,000 cps, preferably from about 5,000 to about 2,000,000 cps, preferably from about 20,000 to about 1,000,000 cps, preferably from about 25,000 to about 750,000 cps and preferably from about 50,000 to about 500,000 cps, including all ranges and subranges therebetween.

Preferably, petrolatum and dimethicone are present in compositions of the present invention in a weight ratio of from 2:1 to 1:2, preferably from 1.5:1 to 1:1.5, preferably from 1.25 to 1:1.25, and preferably about 1:1, including all ranges and subranges therebetween.

Preferably, the total combined amount of dimethicone and petrolatum present in the compositions of the present invention is less than 20% by weight, preferably less than about 15% by weight, preferably less than about 12% by weight, but greater than about 2% by weight, preferably greater than about 5% by weight, and preferably greater than about 8% by weight, all weights being based on the total weight of the composition, including all ranges and subranges such as, for example, from about 7% to about 13% by weight and from about 9% to about 11% by weight, with about 10% being a preferred amount.

Preferably, the compositions of the present invention possess an occlusion component consisting essentially of petrolatum and dimethicone.

as, for example, from about 0.1% to less than 1% by weight and from about 0.3% to about 0.5% by weight, with about 0.4% being a preferred amount.

Ceramide

According to the present invention, compositions comprising at least one ceramide are provided.

Ceramides are a family of bioactive sphingolipids, some of which are found in the stratum corneum. Naturally-occurring ceramides are derived primarily from bovine sources and can be used in the compositions of the present invention. However, synthetic ceramides, also known as pseudoceramides, can also be used. Pseudoceramides are relatively inexpensive, synthetic mimics of natural ceramides. Thus, the compositions of the present invention can contain at least one natural ceramide, at least one pseudoceramide, or both.

Suitable examples of natural ceramides include, but are not limited to, N-(triacontanoyl-☐-O-linoleyl)-sphingosine (ceramide 1), N-(stearoyl)-sphingenine (ceramide 2), N-(stearoyl)-4-hydroxysphingenine (ceramide 3), N-(triacontanoyl-w-O-linoleyl)-6-hydroxysphingosine (ceramide 4), N-(2-hydroxystearoyl)-sphingenine (ceramide 5), N-(2-hydroxystearoyl)-4-hydroxysphingenine (ceramide 6), N-(2-hydroxystearoyl)-6-hydroxysphingenine (ceramide 7), and N-(stearoyl)-6-hydroxysphingenine (ceramide 8).

Suitable examples of pseudoceramides include, but are not limited to ceramide PC-104 [N-(3-hexadecyloxy-2-hydroxypropyl)-N-2-hydroxyethylhexadecanamide] and ceramide Bio391 [N-(2-hydroxyethyl)-2-pentadecanolylhexadecanamide].

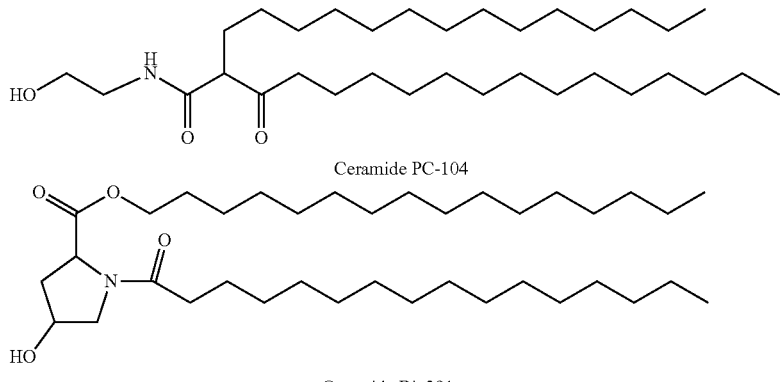

Ceramide PC-104

Ceramide Bio391

Glycerrhetinic Acid

According to the present invention, compositions comprising glycerrhetinic acid are provided.

Glycerrhetinic acid (enoxolone) is a pentacyclic triterpenoid obtained upon hydrolysis of glycyrrhizic acid extracted from *Glycyrrhiza glabra* L. (liquorice) roots. Preferably, glycerrhetinic acid itself is present as an ingredient in the compositions of the present invention. However, it may also be present as part of a mixture of ingredients or an extract such as, for example, licorice extract.

Preferably, glycerrhetinic acid is present in an amount less than 1% by weight, preferably less than about 0.75% by weight, preferably less than about 0.5% by weight, but greater than about 0.1% by weight, preferably greater than about 0.2% by weight, and preferably greater than about 0.3% by weight, all weights being based on the total weight of the composition, including all ranges and subranges such Preferably, compositions of the present invention possess ceramide PC-104.

Preferably, the at least one ceramide is present in an amount less than 1% by weight, preferably less than about 0.8% by weight, preferably less than about 0.6% by weight, but greater than about 0.1% by weight, preferably greater than about 0.2% by weight, and preferably greater than about 0.4% by weight, all weights being based on the total weight of the composition, including all ranges and subranges such as, for example, from about 0.1% to less than 1% by weight and from about 0.4% to about 0.6% by weight, with about 0.5% being a preferred amount.

Preferably, ceramide and glycerrhetinic acid are present in compositions of the present invention in a weight ratio of from 2:1 to 1:2, preferably from 1.5:1 to 1:1.5, preferably from 1.25 to 1:1.25, and preferably about 1:1, including all ranges and subranges therebetween. It is preferred that more ceramide is present in the compositions of the present invention than glycerrhetinic acid.

Preferably, the compositions of the present invention possess a stratum corneum water-holding-ability component consisting essentially of at least one ceramide.

C2-C5 Alkanols Substituted with Two to Four Hydroxyl Groups

According to the present invention, compositions comprising at least one C2-C5 alkanol substituted with two to four hydroxyl groups are provided.

Suitable examples of C2-C5 alkanol substituted with two to four hydroxyl groups include, but are not limited to, such as, for example, propylene glycol, butylene glycol and glycerol (glycerin).

Preferably, C2-C5 alkanol substituted with two to four hydroxyl groups is present in an amount less than 20% by weight, preferably less than about 12% by weight, preferably less than about 8% by weight, but greater than about 1% by weight, preferably greater than about 5% by weight, and preferably greater than about 7% by weight, all weights being based on the total weight of the composition, including all ranges and subranges such as, for example, from about 1% to less than 20% by weight and from about 7% to about 8% by weight, with about 7.5% being a preferred amount.

Preferably, the compositions of the present invention possess a C2-C5 alkanol substituted with two to four hydroxyl groups component consisting essentially of glycerol and propylene glycol. Preferably, propylene glycol and glycerol are both present in compositions of the present invention, and propylene glycol and glycerol are present in a weight ratio of from 5:1 to 1:1, preferably from 4.5:1 to 1.5:1, preferably from 4:1 to 3:1, and preferably about 3.4:1, including all ranges and subranges therebetween.

N-Acylethanolamine

According to the present invention, compositions comprising at least one N-acylethanolamine are provided. Preferably, the N-acylethanolamine is palmitamide MEA (Palmitoylethanolamine or PEA), which has the following structure:

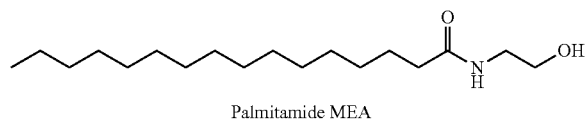 [SMILES: CCCCCCCCCCCCCCCC(=O)NCCO]

Palmitamide MEA

Preferably, at least one N-acylethanolamine is present in an amount less than 1% by weight, preferably less than about 0.05% by weight, preferably less than about 0.03% by weight, but greater than about 0.001% by weight, preferably greater than about 0.004% by weight, and preferably greater than about 0.008% by weight, all weights being based on the total weight of the composition, including all ranges and subranges such as, for example, from about 0.001% to less than 1% by weight and from about 0.008% to about 0.03% by weight, with about 0.01% being a preferred amount.

Preferably, the compositions of the present invention possess an itch reduction component consisting essentially of at least one N-acylethanolamine, in particular palmitamide MEA.

Grape Seed Extract Comprising at Least One Proanthocyanidin

According to the present invention, compositions comprising grape seed extract comprising at least one proanthocyanidin are provided. Suitable grape seed extract for use in the compositions of the present invention contain at least one proanthocyanidin, which are compounds belonging to a class of polyphenols found in a variety of plants. Preferably, at least one proanthocyanidin is present as part of a mixture of ingredients or an extract such as, for example, grape seed extract. However, the at least one proanthocyanidin itself may be present in the composition, such as proanthocyanidins extracted from grape seeds and skin of *Vitis vinifera*, and such extracted proanthocyanidins may be considered part of a grape seed extract.

Preferably, grape seed extract comprising proanthocyanidin is present in an amount less than 1% by weight, preferably less than about 0.5% by weight, preferably less than about 0.2% by weight, but greater than about 0.001% by weight, preferably greater than about 0.01% by weight, and preferably greater than about 0.05% by weight, all weights being based on the total weight of the composition, including all ranges and subranges such as, for example, from about 0.001% to less than 1% by weight and from about 0.05% to about 0.2% by weight, with about 0.1% being a preferred amount.

Preferably, the compositions of the present invention possess an inflammation reduction component consisting essentially of grape seed extract comprising proanthocyanidin, glycerrhetinic acid, and at least one N-acylethanolamine (in particular palmitamide MEA).

Additional Additives

The compositions of the present invention can also comprise any additive usually used in the field of dermatology. For example, sunscreens, preserving agents, fillers, neutralizing agents, film forming agents, dermatological active agents such as, for example, emollients, moisturizers, vitamins, essential fatty acids, surfactants, silicone elastomers, thickening agents, gelling agents, and viscosity increasing agents can be added (or excluded). A person of ordinary skill in the art will take care to select the optional additional additives and/or the amount thereof such that the advantageous properties of the composition according to the invention are not, or are not substantially, adversely affected by the envisaged addition.

These substances may be selected variously by one or ordinary skill in the art in order to prepare a composition which has the desired properties.

For example, compositions of the present invention may optionally include at least one pH adjuster such as a base or acidifying agent.

Examples of suitable bases include, but are not limited to, alkyl amines comprising an alkyl group with 1 to 6 carbon atoms, preferably 2 to 6 carbon atoms, and preferably 2 to 3 carbon atoms; alkanolamines comprising an alkyl group with 1 to 6 carbon atoms, preferably 2 to 6 carbon atoms, and preferably 2 to 3 carbon atoms; basic amino acids; hydroxides of alkali metals; and hydroxides of an alkaline earth metals.

Specific examples of alkyl amines include, but are not limited to, methylamine, ethylamine, propylamine, butylamine, hexylamine, dimethylamine and diethylamine. Specific examples of alkanolamines include, but are not limited to, monoethanolamine, diethanolamine, triethanolamine, N-methyldiethanolamine, N,N-dimethylmonoethanolamine and aminomethyl propanol. Specific examples of basic amino acids include lysine, histidine and arginine. Specific examples of alkali metals include, but are not limited to, sodium hydroxide, potassium hydroxide, and lithium hydroxide. Specific examples of hydroxides of an alkaline earth metals include, but are not limited to, calcium hydroxide and magnesium hydroxide.

If present, at least one pH adjuster can be present in the compositions of the present invention in an amount ranging from about 0.1% to about 3% by weight, preferably about 0.5% to about 2% by weight, and preferably from 0.75% to 1.25% by weight, including all ranges and subranges therebetween, with all weights being based on the total weight of the composition.

Compositions of the present invention may optionally include at least one thickening agent.

Suitable thickening agents include non-ionic thickening agents, cationic thickening agents, and anionic thickening agents. Specific examples of suitable thickening agents include polyacrylamide polymers, polysaccharides, natural or synthetic gums, such as methyl hydroxypropyl cellulose, xanthan gum, polysaccharide gum, hydroxyl propyl cellulose, hydroxyl propyl methyl cellulose, and hydroxyl ethyl cellulose and carboxyvinyl polymers.

If present, the at least one thickening agent can be present in the compositions of the present invention in an amount ranging from about 0.1% to about 5% by weight, preferably about 0.5% to about 1% by weight, and preferably from 0.6% to 0.8% by weight, including all ranges and subranges therebetween, with all weights being based on the total weight of the composition.

Compositions of the present invention may optionally include at least one emulsifying agent.

Suitable emulsifying agents include non-ionic emulsifying agents, cationic emulsifying agents, and anionic emulsifying agents. If the composition of the present invention is an emulsion, the emulsifying agents used in the composition can have HLB values to facilitate production of the desired emulsion. "HLB" refers to the "hydrophilic-lipophilic balance" associated with emulsifying agents. In particular, "HLB" value relates to the ratio of hydrophilic groups and lipophilic groups in emulsifiers, and also relates to solubility of the emulsifiers. Lower HLB emulsifiers are more soluble in oils (lipophilic material) and are more appropriate for use in water-in-oil (W/O) emulsions. Higher HLB emulsifiers are more soluble in water (hydrophilic material) and are more appropriate for oil-in-water (O/W) emulsions.

Suitable examples of emulsifying agents include, but are not limited to, fatty alcohols, fatty acids, and esters thereof, optionally alkoxylated (ethoxylated, propoxylated, etc.) and/or pegylated. Fatty acids correspond to the formula R—COOH and fatty alcohols correspond to the formula R—OH, in which R denotes a saturated or unsaturated hydrocarbon radical preferably having from 7 to 45 carbon atoms, preferably from 9 to 35 carbon atoms, preferably from 15 to 35 carbon atoms, preferably from 15 to 21 carbon atoms, and preferably from 16 to 18 carbon atoms. Mention may be made of, for example, lauric acid/alcohol, stearic acid/alcohol, oleic acid/alcohol, behenyl acid/alcohol, cetyl acid/alcohol and mixtures thereof (including ceteareth compounds).

Suitable emulsifiers include ethoxylated fatty alcohols, ethoxylated fatty acids, partial glycerides of ethoxylated fatty acids, polyglycerolated fatty acid triglycerides and ethoxylated derivatives thereof, and mixtures thereof. Specific examples include: Glyceryl Stearate; Sorbitan Isostearate; Oleth-2; Ceteth-2; Methyl Glucose Sesquistearate; Laureth-4; Cetearyl Glucoside; Polysorbate 85; Ceteth-10; Cocamide MEA; C12-14 pareth-12; Polysorbate 60; Isosteareth-20; PEG-20 Methyl Glucose Sesquistearate; Polysorbate 80; Stearic Acid; Cetyl alcohol; Behenyl alcohol; Cetearyl alcohol; Ceteth-20; Polysorbate 20; Laureth-23; PEG-100 Stearate and Sodium lauryl sulfate.

If present, the at least one emulsifying agent can be present in the compositions of the present invention in an amount ranging from about 1% to about 20% by weight, preferably about 4% to about 15% by weight, and preferably from 7% to 9% by weight, including all ranges and subranges therebetween, with all weights being based on the total weight of the composition.

Compositions of the present invention may optionally include at least one preservative.

Suitable preservatives are known in the art and include, but are not limited to, phenonip XB (phenoxyethanol), chlorhexidine, ethylparaben, propylparaben methylparaben, EDTA or salts thereof (e.g. disodium EDTA), DMDM hydantoin, and the like.

If present, the at least one preservative can be present in the compositions of the present invention in an amount ranging from about 0.01% to about 3% by weight, preferably about 0.1% to about 1.5% by weight, and preferably from 0.4% to 0.6% by weight, including all ranges and subranges therebetween, with all weights being based on the total weight of the composition.

According to the present invention, particularly preferred compositions include the following compositions:

| Ingredient | Amount (wt %) |
| --- | --- |
| Thickening agent | 0.6-0.8 |
| Surfactant | 7-9 |
| C2-C5 alkanol substituted with two to four hydroxyl groups | 7-8 |
| Preservative | 0.4-0.6 |
| pH adjuster | 0.75-1.25 |
| Dimethicone | 4-6 |
| Petrolatum | 4-6 |
| Ceramide | 0.4-0.6 |
| N-acylethanolamine | 0.008-0.03 |
| Glycerrhetinic acid | 0.3-0.5 |
| Grape seed extract | 0.05-0.2 |
| Purified water | QS to 100 |

According to the present invention, particularly preferred compositions include the following compositions:

| Ingredient | Amount (wt %) |
| --- | --- |
| Carbomer 980 | About 0.7 |
| Stearic acid | About 6.25 |
| Glycerin | About 1.7 |
| Propylene glycol | About 5.8 |
| Polysorbate 20 | About 1.4 |
| Triethanolamine | About 1 |
| Phenonip XB | About 0.5 |
| Sodium hydroxide | About 0.008 |
| Dimethicone | About 5 |
| Petrolatum | About 5 |
| Ceramid PC-104 | About 0.5 |
| Palmitamide MEA | About 0.01 |
| Glycerrhetinic acid | About 0.4 |
| Grape seed extract | About 0.1 |
| Purified water | QS to 100 |

According to preferred embodiments of the present invention, methods of treating one or more skin dermatoses, in particular atopic dermatitis and/or allergic contact dermatitis, comprising topically administering compositions comprising water, petrolatum, dimethicone, glycerrhetinic acid, at least one ceramide, at least one C2-C5 alkanol substituted with two to four hydroxyl groups, at least one N-acylethanolamine, and grape seed extract comprising at least one proanthocyanidin to the one or more skin dermatoses in an amount sufficient to treat the one or more skin dermatoses are provided. In accordance with the preceding methods, the compositions of the present invention are applied topically to the desired area of the skin (one or more dermatoses) in an amount sufficient to treat the dermatoses. The compositions may be applied to the desired area as needed, preferably one to four times daily, preferably two to three times daily, and preferably three times daily. During application, the composition is preferably rubbed on the desired area until the composition has been absorbed by the skin. Preferably, the desired area of skin is cleaned prior to application.

According to preferred embodiments of the present invention, methods of reducing at least one symptom associated with one or more skin dermatoses, in particular atopic dermatitis and/or allergic contact dermatitis, comprising topically administering compositions comprising water, petrolatum, at least one dimethicone, glycerrhetinic acid, at least one ceramide, at least one C2-C5 alkanol substituted with two to four hydroxyl groups, at least one N-acylethanolamine, and grape seed extract comprising at least one proanthocyanidin to the one or more skin dermatoses in an amount sufficient to reduce the at least one symptom associated with the one or more skin dermatoses are provided. Symptoms associated with the one or more dermatoses include erythema (redness), pruritus (itchiness), excoriation (scratches, scabs), papulation (bumpiness), edema (swelling), and/or oozing.

In accordance with the preceding methods, the compositions of the present invention are applied topically to the desired area of the skin (one or more dermatoses) in an amount sufficient to reduce the at least one symptom associated with the one or more skin dermatoses. The compositions may be applied to the desired area as needed, preferably one to four times daily, preferably two to three times daily, and preferably three times daily. During application, the composition is preferably rubbed on the desired area until the composition has been absorbed by the skin. Preferably, the desired area of skin is cleaned prior to application.

Also in accordance with all of the preceding methods, compositions of the present invention are preferably contained in a suitable container for dermatological compositions. Suitable shapes of such containers include, but are not limited to, any geometric shape such as, for example, tube-shaped, square, rectangular, pyramidal, oval, circular, hemispherical, etc. Further, the container may be made of flexible or inflexible material.

Preferably, either (1) the container contains a pump top which allows product to be deposited into hands for application; or (2) the container does not contain any top, and product is deposited into hands for application by squeezing the container. Preferably, a pump top is present.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Composition of the Present Invention

| Ingredient | Function | Amount (wt %) |
|---|---|---|
| Carbomer 980 | Thickening agent | 0.7 |
| Stearic acid | Emulsifying agent | 6.25 |
| Glycerin | Humectant | 1.7 |
| Propylene glycol | Humectant | 5.8 |
| Polysorbate 20 | Emulsifying agent | 1.4 |
| Triethanolamine | Emulsifying agent and pH buffer | 1 |
| Phenonip XB | Preservative | 0.5 |
| Sodium hydroxide | pH adjuster | 0.008 |
| Dimethicone | Occlusive Agent | 5 |
| Petrolatum | Occlusive Agent | 5 |
| Ceramid PC-104 | Skin conditioning agent | 0.5 |
| Palmitamide MEA | Viscosity builder; skin conditioning agent | 0.01 |
| Glycerrhetinic acid | Skin conditioning agent | 0.4 |
| Grape seed extract | Antioxidant | 0.1 |
| Purified water | Solvent | QS to 100 |

What is claimed is:

1. A composition comprising water, from about 1% to about 10% by weight of petrolatum, from about 1% to about 10% by weight of dimethicone, from about 0.1% to about 1% by weight of glycerrhetinic acid, from about 0.1% to about 1% by weight of at least one ceramide, from about 1% to about 20% by weight of at least one C2-C5 alkanol substituted with two to four hydroxyl groups, from about 0.001% to less than 1% by weight of at least one N-acylethanolamine, and from about 0.001% to less than 1% by weight of grape seed extract comprising proanthocyanidin, all weights being based on the total weight of the composition.

2. The composition of claim 1, wherein the composition is free of film forming agents.

3. The composition of claim 1, wherein the composition is free of homopolymers of polyvinylpyrrolidone.

4. The composition of claim 1, wherein petrolatum and dimethicone are present in compositions of the present invention in a weight ratio of about 1:1.

5. The composition of claim 1, wherein the composition comprises an occlusion component consisting essentially of petrolatum and dimethicone.

6. The composition of claim 1, wherein the ceramide is ceramide PC-104.

7. The composition of claim 1, wherein ceramide and glycerrhetinic acid are present in compositions of the present invention in a weight ratio of about 1:1.

8. The composition of claim 1, wherein the composition comprises a stratum corneum water-holding-ability component consisting essentially of at least one ceramide.

9. The composition of claim 1, wherein the composition comprises a C2-C5 alkanol substituted with two to four hydroxyl groups component consisting essentially of glycerol and propylene glycol in a weight ratio of from 4:1 to 3:1.

10. The composition of claim 1, wherein the N-acylethanolamine is palmitamide MEA.

11. The composition of claim 1, wherein the composition comprises an itch reduction component consisting essentially of palmitamide MEA.

12. The composition of claim 1, wherein the composition comprises an inflammation reduction component consisting essentially of grape seed extract comprising proanthocyanidin, glycerrhetinic acid, and palmitamide MEA.

13. A composition consisting of:

| Ingredient | Amount (wt %) |
|---|---|
| Thickening agent | 0.6-0.8 |
| Surfactant | 7-9 |
| Polyol humectant | 7-8 |
| Preservative | 0.4-0.6 |
| pH adjuster | 0.75-1.25 |
| Dimethicone | 4-6 |
| Petrolatum | 4-6 |
| Ceramide | 0.4-0.6 |
| N-acylethanolamine | 0.008-0.03 |
| Glycerrhetinic acid | 0.3-0.5 |
| Grape seed extract | 0.05-0.2 |
| Purified water | QS to 100. |

14. A composition consisting of:

| Ingredient | Amount (wt %) |
|---|---|
| Carbomer 980 | About 0.7 |
| Stearic acid | About 6.25 |
| Glycerin | About 1.7 |
| Propylene glycol | About 5.8 |
| Polysorbate 20 | About 1.4 |
| Triethanolamine | About 1 |
| Phenonip XB | About 0.5 |
| Sodium hydroxide | About 0.008 |
| Dimethicone | About 5 |
| Petrolatum | About 5 |
| Ceramid PC-104 | About 0.5 |
| Palmitamide MEA | About 0.01 |
| Glycerrhetinic acid | About 0.4 |
| Grape seed extract | About 0.1 |
| Purified water | QS to 100. |

15. A method of treating one or more skin dermatoses and/or reducing at least one symptom associated with one or more skin dermatoses comprising topically administering the composition of claim 1 to the one or more skin dermatoses in an amount sufficient to treat the one or more skin dermatoses and/or reduce at least one symptom associated with the one or more skin dermatoses.

16. A method of treating one or more skin dermatoses and/or reducing at least one symptom associated with one or more skin dermatoses comprising topically administering the composition of claim 13 to the one or more skin dermatoses in an amount sufficient to treat the one or more skin dermatoses and/or reduce at least one symptom associated with the one or more skin dermatoses.

17. A method of treating one or more skin dermatoses and/or reducing at least one symptom associated with one or more skin dermatoses comprising topically administering the composition of claim 14 to the one or more skin dermatoses in an amount sufficient to treat the one or more skin dermatoses and/or reduce at least one symptom associated with the one or more skin dermatoses.

* * * * *